United States Patent [19]
Krah

[11] Patent Number: 5,408,185

[45] Date of Patent: Apr. 18, 1995

[54] APPARATUS FOR AUTOMATED POLYELECTROLYTE MEASUREMENT

[75] Inventor: Robert Krah, Ottobrunn, Germany

[73] Assignee: Mütek GmbH, Herrsching, Germany

[21] Appl. No.: 923,972

[22] PCT Filed: Mar. 8, 1991

[86] PCT No.: PCT/EP91/0041

§ 371 Date: Nov. 18, 1992

§ 102(e) Date: Nov. 18, 1992

[87] PCT Pub. No.: WO92/15281

PCT Pub. Date: Sep. 17, 1992

[30] Foreign Application Priority Data

Mar. 20, 1990 [DE] Germany .................. 40 08 916.9

[51] Int. Cl.$^6$ .................................. G01N 27/60
[52] U.S. Cl. .................... 324/453; 324/446; 324/71.1; 204/194
[58] Field of Search ............... 324/453, 439, 445, 446, 324/450, 452, 71.1; 134/143, 184; 204/193, 194, 280; 73/864.16, 864.34

[56] References Cited

U.S. PATENT DOCUMENTS

| | | | |
|---|---|---|---|
| 3,368,145 | 2/1968 | Gerdes | 324/32 |
| 3,421,855 | 1/1969 | Kateman et al. | 23/230 |
| 3,526,827 | 9/1970 | Cardwell | 324/453 |
| 4,446,435 | 5/1984 | Canzoneri | 324/453 |
| 4,449,101 | 5/1984 | Canzoneri et al. | 324/453 |
| 4,769,608 | 9/1988 | Bryant | 324/453 |
| 4,825,169 | 4/1989 | Carver | 324/453 |
| 4,961,147 | 10/1990 | Moore | 324/453 |
| 5,220,283 | 6/1993 | Dentel | 324/453 |

OTHER PUBLICATIONS

"12th Material ISA Analysis Instr., vol. 4 Symposium, Houston, Tex. 1966: pp. 181–198".

Primary Examiner—Kenneth A. Wieder
Assistant Examiner—Jay M. Patidar
Attorney, Agent, or Firm—Marshall, O'Toole, Gerstein, Murray & Borun

[57] ABSTRACT

Apparatus for automated polyelectrolyte measurement of liquid process materials including a sample vessel which defines an electrically insulating, cylindrical cavity below a larger-diameter reservoir. Electrodes are located at the ends of the cylindrical cavity and an insulating piston is reciprocated with a predetermined, small clearance within the cavity. The charge displacement is measured between the electrodes. An outlet channel opening at the floor of the cylindrical cavity is connected to an outlet pipe. A rinsing duct with valve control for introducing a rinsing fluid into the reservoir. A controller is connected to an actuator for reciprocating the piston, to a valve in the outlet pipe and to the rinsing valve. After each polyelectrolyte measurement the substance under test is removed from the sample vessel through the outlet channel, rinsing fluid is introduced, and the rinsing fluid is removed through the outlet channel while the piston reciprocates. The reciprocation of the piston provides a pumping action which is used to expel the substance under test and enables effective rinsing and cleaning of the apparatus with no need for manual intervention.

15 Claims, 2 Drawing Sheets

APPARATUS FOR AUTOMATED POLYELECTROLYTE MEASUREMENT

FIELD OF THE INVENTION

The present invention relates to an apparatus for automated polyelectrolyte measurement.

DESCRIPTION OF THE PRIOR ART

In the U.S. publication "12th Material ISA Analysis Instr. Symposium, Houston, Tex., 1966: Vol. 4, pp 181–198" apparatus of the same kind as that of the present invention is described. However, this apparatus has been designed not for automated polyelectrolyte measurement but rather as a device for purely manual operation. Hence, with the said device samples taken for measurement of the polyelectrolyte consumption in a process are introduced by hand into a sample vessel and a piston is moved so as to generate a streaming potential which is recorded and measured by electrodes, a titration operation being carried out at the same time. After the measurement has been taken in this way, which is a conventional procedure, the piston is withdrawn from the sample vessel and the sample is removed. The piston and the sample vessel are then cleaned so as to be ready for a subsequent measurement procedure.

In many cases polyelectrolyte consumption must be monitored in the course of an industrial chemical process in order to regulate that process. Examples of such processes include the manufacture of paper, the disposal of aqueous waste and similar processes in which flocculents, for instance, are employed. These processes have always required the continual presence of a worker to carry out the necessary measurements, the results of which are needed for regulating the process. This sort of purely manual measurement has the disadvantages of, on the one hand, being labor-intensive and, on the other, of often not making the results of the measurement available soon enough to regulate or control the process correctly.

SUMMARY OF THE INVENTION

The object of the present invention is directed to provide an apparatus by means of which polyelectrolyte measurement can be carried out automatically in a simple and reproducible way.

According to the present invention there is provided an apparatus for automated polyelectrolyte measurement of a substance comprising a sample vessel defining an electrically insulating cylindrical cavity and provided with a reservoir of larger diameter than said cylindrical cavity and located above and in communication with said cavity, electrodes located substantially at the ends of said cylindrical cavity respectively, an electrically insulating piston, which defines a predetermined clearance with walls defining said cylindrical cavity, an actuating means for reciprocating said piston within said cylindrical cavity and a means of measuring a charge displacement between said electrodes, and wherein the improvement comprises the provision of an outlet arrangement located at the bottom of said cylindrical cavity, a first valve for the control of fluid through said outlet arrangement, a rinsing duct for the introduction of a rinsing fluid into said reservoir, a second valve located in said rinsing duct to control the flow of said rinsing fluid through said rinsing duct, and a controller which is connected to and can control operation of said actuating means, said first valve and said second valve so that after a polyelectrolyte measurement has been carried out, the substance under test can be expelled from said cylindrical cavity through the outlet arrangement and said rinsing fluid can be introduced into said reservoir and thence expelled through the outlet arrangement as said piston is reciprocated.

Thus the advantage of the invention is that the movement of the piston, which is necessary for the purpose of measurement, is combined with the operation of the valve in the outflow arrangement and the positioning of the outlet channel so that it opens at the floor of the cylindrical section, in such a way as to provide a pumping action which enables effective rinsing and cleaning of the apparatus with no need for manual intervention. This pumping action further serves to expel the process material being tested, which results in an independently controlled, automatically operating arrangement.

It should be noted that the rinsing of an analysis vessel for measurement of the conductance of a medium by a piston/cylinder arrangement with moving piston is described in German patent Specification DE-AS 25 21 009. Here, however, the medium to be measured is itself used as the rinsing medium and furthermore it is not drained off through a separate outlet. Instead, the whole arrangement is dipped into the liquid to be tested in such a way that the liquid is both drawn in and expelled through an annular gap between piston and cylinder at the top of the apparatus.

To achieve precise regulation it is an advantage for the drive mechanism to include a position sensor to monitor the position of the piston. Where the piston is reciprocated by a crank mechanism, a suitable instrument is an angle indicator that signals the crank rotation.

In order to clean the apparatus it advantageous to couple an ultrasonic oscillator mechanically to the sample vessel, so that during the rinsing process the rinsing fluid can be set into oscillation by way of the sample vessel. In this way particles adhering to the surfaces of the vessel are removed primarily by a cavitation effect.

Thus, it is advantageous for the floor of the sample vessel to consist of metal, which provides a zero-loss coupling of the ultrasonic oscillations to the liquid, as opposed to coupling by way of insulating surfaces made of plastic which would involve an excessive attenuation. Impedance-matching is preferably achieved by constructing the portion of the vessel defining the floor with a flared cross-section.

The sample vessel preferably comprises an outer vessel made of metal which defines a substantially cylindrical interior cavity into which is shrink-fitted an insulating block. The insulating block, which preferably consists of polytetrafluoroethylene, defines an open bore with an upper section forming the reservoir, a graduated transition portion, and a lower cylindrical section defining said cavity. In the bottom surface of the insulating block a channel is cut which, when closed off by the flat floor of the outer vessel, forms a duct. This arrangement makes it possible to empty the sample vessel completely so that there is hardly any residual rinsing fluid can remain to contaminate a subsequent sample.

It is particularly advantageous for the apparatus to incorporate a sampling device comprising a pumping means connected on its input side to a suction pipe, through which the process material to be tested can be sucked in. On its output side the pumping means communicates through a pressure pipe with a first input of a valve, by means of which a sampling container can be connected either with the pressure pipe or with a source of compressed gas. The other end of the sampling tube is connected by way of a further valve either to a source of the process substance to be tested or to the reservoir. In operation, the process substance is allowed to flow through the sampling tube so that the latter is constantly filled with a sample representative of the momentary situation. Whenever it is desired to withdraw a sample from the tube and subsequently determine its polyelectrolyte content, the valves are switched so that the compressed gas impinges on the contents of the sampling tube and pushes them into the reservoir section. This arrangement ensures that the amount of liquid in the sample is reproducible and simultaneously avoids the risk of contaminating the sample.

DESCRIPTION OF THE PREFERRED EMBODIMENTS

Figure 1:
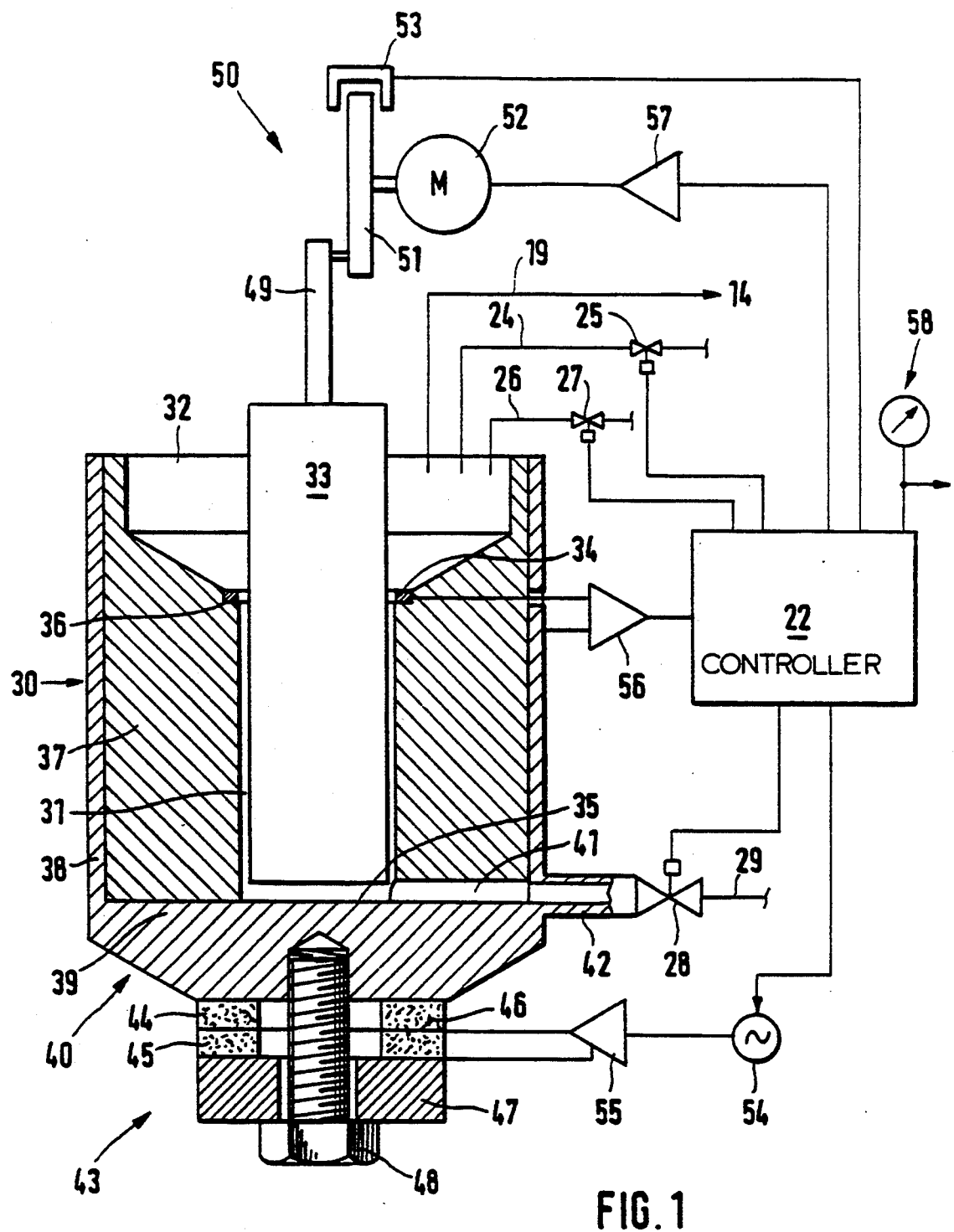
FIG. 1 is a diagrammatic partial longitudinal section through one embodiment of apparatus in accordance with the invention.

In the embodiment of the invention shown in FIG. 1, a sample vessel 30 is provided, which comprises an inner insulating block 37 and an outer metal part consisting of an outer wall 38 and a floor 39. Preferably, the block 37 is made from polytetrafluoroethylene and the vessel 30 is made from V2A grade stainless steel, as defined in the standard German "Stahl Schlüssel".

A bore formed substantially in the middle of the insulating block 37 defines a cylindrical cavity 31, the upper end of which is continuous with a larger-diameter, also cylindrical reservoir 32. At the upper end of the cylindrical cavity 31 there is an annular indentation 36, within which is fixed an annular first electrode 34 made of a non-corroding metal. The floor 39 closes off the cylindrical cavity 31 at its lower end and forms a second electrode 35 at this site.

The electrodes 34 and 35 are connected to the inputs of an amplifier 56, the output of which is connected to an input of a control mechanism 22.

The floor 39 is integral with a flared section 40, to the end of which are attached two annular piezo oscillators 44,45 which are stacked one above the other and pressed against the floor by means of a screw bolt 48 and a washer 47. Between the piezo rings 44 and 45 is inserted an electrode 46. The arrangement is such that the outer annular surfaces of the piezo rings 44, 45 are in electrical contact with one another by way of the bolt 48, so that the piezo rings 44, 45 are electrically in parallel and mechanically in series. They are controlled electrically by way of the electrode 46 and the metal parts 39/40, 47 and 48, by an ultrasound generator 54 the output of which is passed through a driver amplifier 55. The whole arrangement preferably includes feedback so that the oscillation frequency is automatically set to a value that is optimized on the basis of all the electrical and mechanical components. In addition, the flared cross-sectional shape of the section 40 assists in the prevention of excessive attenuation.

In the bottom surface of the insulating block 37 is cut a radial channel 41 to provide a duct with a part circular cross-section, resembling that of a highway tunnel, formed by the walls of the channel and the floor 39. Where the outer end of the channel 41 meets the outer wall 38 there is a hole in the latter adjoining a connection piece 42. To the connection piece 42 is attached a conduit leading to a solenoid valve 28, by way of which the connection piece 42 is connected to an outlet pipe 29. The solenoid valve 28 is connected to the controller 22 by way of a control line.

Inserted into the cylindrical cavity 31 is a piston 33, which is made of an electrically insulating material and is dimensioned so that there is a very narrow gap of the order of a few tenths of a millimeter between the outer surface of the piston 33 and the insulating block 37 defining the walls of the cavity 31. The piston 33 has a planar end surface and at its opposite end is joined by a shaft 49 to a crank 51 that can be rotated by an electrical motor 52. An angle indicator 53 is attached to the crank 51 to monitor the angle of rotation of the crank 51, which is a measure of the vertical position of the piston 33, and to signal it to the controller 22. The motor 52 can be adjusted by the controller 22 by way of a driver amplifier 57, so that the actuation 50 of the piston 33 can be precisely regulated.

There are three inputs to the reservoir section 32. One is a rinsing duct 26, which can be connected to a container filled with a rinsing fluid, such as distilled water, by way of a solenoid valve 27 controlled by the controller 22. A titration duct 24 also opens into the reservoir section 32 and can be connected to a container in which the titration fluid is stored by way of a solenoid valve 25 which, again, is controlled by the controller 22. Finally, a sample of the liquid to be tested is introduced to the sample vessel by a duct 19 that opens into the reservoir section 32. This introduction of a sample is also carried out under the control of the controller 22.

The operation of the above apparatus will now be described.

A predetermined amount of sample liquid is introduced into the reservoir section 32 by way of the duct 19. The piston 33 is reciprocated by the actuating means 50 and the streaming potential so produced is conducted to the controller 22 by way of the electrodes 34, 35 and the amplifier 56. The controller 22 processes the data and indicates or records the measured value by way of a measuring device 58 or makes the measured value available as a control signal to other parts of the system (not shown). At the same time, titration is performed by way of the duct 24.

After the measurement has been completed, the valve 28 is opened during each down stroke of the piston 33 and closed during each up stroke. As a result, all the liquid contained in the vessel is pumped into the outlet pipe 29 and can be discarded. After the pumping has proceeded for a time sufficient to ensure that no appreciable quantity of sample remains in the vessel, the rinsing valve 27 is opened so that rinsing fluid can enter the reservoir section 32 by way of the duct 26. As it does so, the piston 33 continues to reciprocate, the valve 28 opening and closing in synchrony with this motion as described above. At the same time the ultrasound generator 54 is turned on by the controller 22, so that ultrasonic oscillation is induced in the rinsing fluid. By the cavitation action of the ultrasonic oscillation of the fluid, in combination with the flow of the rinsing fluid through the chamber while the piston is moving, the parts that had been in contact with the sample are thoroughly cleaned. The channel 41 is also thoroughly cleaned, because part of its wall is formed by the floor 39, which is set into oscillation by the ultrasonically oscillating unit 43.

When the rinsing process has continued for a sufficient time, the inflow of rinsing fluid is cut off by closing the valve 27, whereupon the rest of the rinsing fluid is pumped out by movement of the piston 33. A new sample can be now be introduced.

In order to take the sample from a process conduit 20, (FIG. 2), or a process vessel it is advantageous to use the apparatus that will now be described with reference to FIG. 2. This apparatus comprises a suction pipe 11, which communicates at one end with the process conduit 20 or with a process vessel, and at the other end with the input side of a pump 10. On its pressure side, the pump 10 is connected by way of a pressure pipe 12 to an input a of a first solenoid valve 13, the output b of which is attached to one end of a sampling tube 15. The other end of the sampling tube 15 is connected to an input b of a second solenoid valve 14, the output a of which communicates with the process conduit 20 or a process vessel by way of a return pipe 16. With the solenoid valves 13, 14 in the states illustrated in the indicated inner diagrams in FIG. 2, liquid is continuously drawn from the process conduit 20 and pumped through the sampling tube 15, so that the contents of the sampling tube 15 are the same as the momentary contents of the process conduit 20. Thus, FIG. 2 illustrates the filling of the sampling tube 15 with fluid from the process conduit 20, when the solenoid valves 13, 14 are in the states illustrated in the indicated inner diagrams in FIG. 2.

A second input c of the first valve 13 is connected to a source of compressed gas 18 by way of a compressed-gas pipe 17. A second output c of the second valve 14 is connected to the sampling pipe 19, which opens into the reservoir section 32. With the solenoid valves 13, 14 in the states indicated in the inner diagrams in FIG. 2, it can be seen that the source of compressed gas 18 is not connected to the sampling tube 15.

Figure 2:
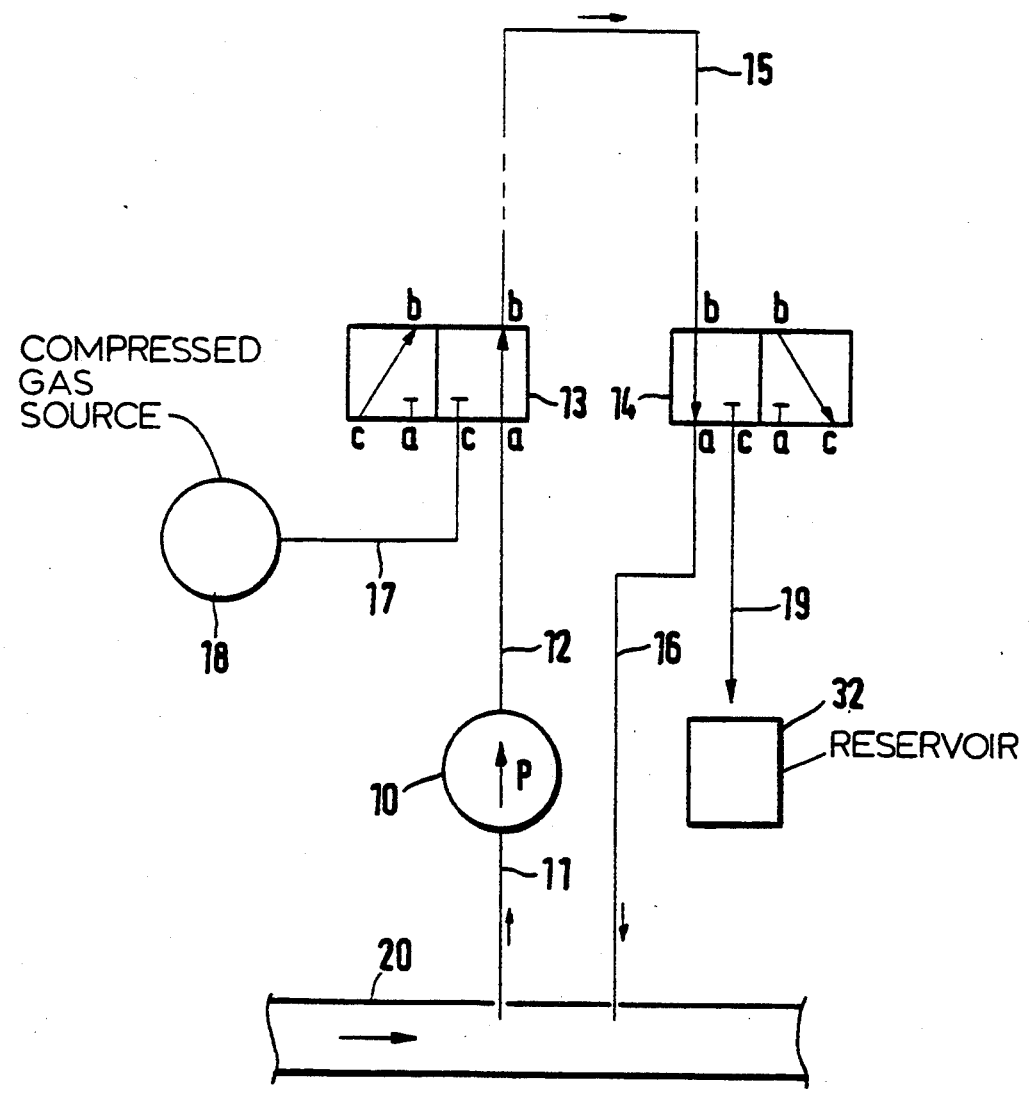
FIG. 2 is a block diagram of an embodiment of a sampling apparatus for use with the apparatus shown in FIG. 1.

When the solenoid valves 13, 14 are switched by the controller 22 to the states shown in the alternate outer diagrams in FIG. 2, the source of compressed gas 18 is connected to the sampling tube 15 so that the contents of the sampling tube 15 and residual contents of the valves 13 and 14 (i.e., any droplet of fluid which may be trapped in the valves) are pushed by compressed gas, from the source 18, through the sampling pipe 19 into the reservoir section 32. The gas is preferably allowed to flow until even the remaining droplets have been introduced into the reservoir section 32. With this method of sampling an unusually precise, reproducible dosage is achieved in the simplest way, with no change in the composition of the sample. Furthermore, the sampling device is invulnerable to liquids otherwise difficult to handle, containing potentially abrasive solids, because all parts are rinsed with an excess of process liquid on the one hand and compressed air on the other hand. This advantage, especially important in monitoring aqueous waste, is complemented by the particularly effective cleansing of the part of the apparatus shown in FIG. 1.

The condition of the surfaces of electrodes 34 and 35 can be monitored by means of the initial potential developed, the fluid remaining substantially constant because the chemical properties of the fluid remain substantially constant such that, when filling the sample vessel 30 with a fresh sample, the same initial potential between the electrodes 34 and 35 can be expected as with the original sample. In another embodiment of the invention, a constant standard fluid having known and constant chemical properties is introduced into the reservoir section 32 instead of a sample, so that the initial potential provides an exact criterion by which to evaluate the surface condition of electrodes 34 and 35. As soon as the initial potential falls below a critical level, the controller 22 actuates a warning system so that the electrodes can be serviced.

What is claimed is:

1. An apparatus for automated polyelectrolyte measurement of a substance comprising:
   a sample vessel defining an electrically insulating cylindrical cavity and a reservoir of larger diameter than said cylindrical cavity and located above and in communication with said cavity;
   a first electrode located substantially at a first end of said cylindrical cavity and a second electrode located at a second end of said cavity;
   an electrically insulating piston, which defines a predetermined clearance with walls defining said cylindrical cavity;
   an actuating means for reciprocating said piston within said cylindrical cavity;
   means for measuring a charge displacement between said first and said second electrodes;
   a fluid outlet located at the bottom of said cylindrical cavity;
   a first valve for controlling fluid through said outlet;
   a rinsing duct for introducing a rinsing fluid into said reservoir;
   a second valve located in said rinsing duct for controlling the flow of said rinsing fluid through said rinsing duct; and
   a controller for controlling the operation of said actuating means, said first valve and said second valve, said controller being adapted to open said first valve during a downward stroke of said piston and to close said first valve during an upward stroke of said piston when, after a polyelectrolyte measurement has been carried out, said substance is expelled from said cylindrical cavity through said outlet.

2. An apparatus as claimed in claim 1, wherein said controller includes means so that during rinsing of said sample vessel, said first valve is opened during downward strokes of said piston and closed during upward strokes of the piston.

3. An apparatus as claimed in claim 1, wherein said actuating means comprises a position sensor to monitor the position of said piston.

4. An apparatus as claimed in claim 1, comprising an ultrasonic oscillator coupled mechanically to said sample vessel and controlled so that ultrasonic oscillation is induced in said rinsing fluid.

5. An apparatus as claimed in claim 4, wherein the bottom of said cylindrical cavity comprises a metal body to which the ultrasonic oscillator is coupled.

6. An apparatus as claimed in claim 5, wherein said metal body is coupled to the ultrasonic oscillator by way of a flared section for impedance matching between said ultrasonic oscillator and said metal body.

7. An apparatus as claimed in claim 6, wherein said metal body is integral with said flared section.

8. An apparatus according to claim 5, wherein said metal body comprises said first electrode.

9. An apparatus as claimed in claim 1, wherein the sample vessel comprises a metallic outer vessel defining a substantially cylindrical interior space into which is fitted an insulating block, said block defining open communicating bores of graded diameter to provide said cylindrical cavity and said reservoir.

10. An apparatus as claimed in claim 9, wherein said outer vessel defines a planar floor perpendicular to the longitudinal axis of the cylindrical space, said outlet arrangement comprises a section outside said vessel which is located at the same level as said floor, said insulating block defining a channel which is oriented radially with respect to the cylindrical interior space of said sample vessel and which faces and is closed off by said floor to define a duct forming an inner part of said outlet arrangement.

11. An apparatus as claimed in claim 9, wherein said insulating block is made of polytetrafluoroethylene.

12. An apparatus as claimed in claim 1, wherein said sample vessel is made of a V2A steel as defined herein.

13. An apparatus as claimed in claim 1, wherein a sampling means is provided for taking samples of a liquid process substance for delivery to said reservoir, said sampling means comprising:
- a suction pipe for connection to a source of said substance under test;
- a pumping means connected on an input side thereof to said suction pipe;
- a pressure pipe connected to an output side of said pumping means;
- a conduit-shaped sampling container;
- a third valve means opening and closing a port between said pressure pipe and a first end of said sampling container;
- a return pipe connected to said source;
- a fourth valve means for opening and closing a port between a second end of said sampling container and said return pipe to flow, when said third and fourth valve means are open, said substance under test from said source through said suction pipe, said pumping means, said pressure pipe, said sampling container and said return pipe back to said source and for entirely filling said sampling container by said substance under test;
- a sampling pipe which opens into said reservoir;
- a fifth valve means for opening and closing a port between said sampling pipe and said second end of said sampling container;
- a compressed gas-pipe connected to a compressed gas-source;
- a sixth valve means for opening and closing a port between said first end of said sampling container and said compressed gas-pipe for supplying when said third and fourth valves are closed and said fifth and sixth valves are open a compressed gas to said sampling container to propel a content of said sampling container through said fifth valve and said sampling pipe into said reservoir.

14. An apparatus as claimed in claim 13, wherein said third and sixth valve means and said fourth and fifth valve means each comprise three-way valves in which first positions connect said pressure pipe to said sampling container and the sampling container to said return pipe, and in second positions connect said compressed gas-pipe to said sampling container and the sampling container to said sampling pipe, respectively.

15. An apparatus as claimed in claim 13, wherein said compressed gas-source comprises a compressed gas-source providing an inert gas under pressure.

* * * * *

UNITED STATES PATENT AND TRADEMARK OFFICE
CERTIFICATE OF CORRECTION

PATENT NO.  :  5,408,185
DATED       :  April 18, 1995
INVENTOR(S) :  Robert Krah It is certified that error appears in the above-identified patent and that said Letters Patent is hereby corrected as shown below:

On the title page, item [86], PCT No.:

change "PCT/EP91/0041" to --PCT/EP91/00441--.

Signed and Sealed this

Second Day of April, 1996

*Attest:*

BRUCE LEHMAN

*Attesting Officer*       Commissioner of Patents and Trademarks